United States Patent [19]
Glock

[11] Patent Number: 5,462,549
[45] Date of Patent: Oct. 31, 1995

[54] FEMORAL SIZING APPARATUS

[75] Inventor: Steven R. Glock, Fort Wayne, Ind.

[73] Assignee: Biomet, Inc., Warsaw, Ind.

[21] Appl. No.: 877,657

[22] Filed: May 1, 1992

[51] Int. Cl.$^6$ .................................................. A61F 5/00
[52] U.S. Cl. ........................................... 606/86; 606/88
[58] Field of Search ................................ 606/79, 81, 82, 606/86, 87, 88, 89, 96, 97, 98

[56] References Cited

U.S. PATENT DOCUMENTS

| | | | |
|---|---|---|---|
| 4,211,228 | 7/1980 | Cloutier | 606/88 |
| 4,467,801 | 8/1984 | Whiteside . | |
| 4,567,885 | 2/1986 | Androphy | 606/88 |
| 4,646,729 | 3/1987 | Kenna | 606/88 |
| 4,653,488 | 3/1987 | Kenna | 606/88 |
| 4,703,751 | 11/1987 | Pohl | 606/87 |
| 4,718,413 | 1/1988 | Johnson | 606/82 |
| 4,759,350 | 7/1988 | Dunn | 606/82 |
| 4,791,919 | 12/1988 | Elloy | 606/82 |
| 5,035,700 | 7/1991 | Kenna | 606/87 |
| 5,053,037 | 10/1991 | Lackey | 606/79 |

OTHER PUBLICATIONS

BIOMET, Inc. AGC Total Knee System "Patellar Femoral Systems".
BIOMET, Inc., AGC Total Knee System "Surgical Overview Featuring Accu–Line Knee Instrumentation".
ORTHOMET, Inc., "Orthomet PLUS Total Knee System".
DePUY, "The AMK Total Knee System" Design Rationale and Surgical Procedure pp. 18–19.
BIOMET, Inc., AGC Total Knee System "Revision Surgical Overview".
BIOMET, Inc. "Surgical Technique for the AGC Total Knee System".
BIOMET, Inc., "Extramedullary Surgical Technique".
BIOMET, Inc., "Intramedullary with Distractor Surgical Overview".
BIOMET, Inc., "Intramedullary without Distractor surgical Overview".
BIOMET, Inc., "Extramedullary Surgical Overview".

*Primary Examiner*—Michael A. Brown
*Attorney, Agent, or Firm*—George Pappas

[57] ABSTRACT

A femoral sizing apparatus includes a plurality of flat templates, each having specific anterior to posterior first dimensions and medial to lateral second dimensions. Each of the plurality of plates correspond to a specific femoral component size. A handle is attached to each of the templates and is used for lifting and placing the plate against the distal femur after the distal femoral cut is made. When the template is placed against the distal femur, both the anterior to posterior dimension and the medial to lateral dimension are considered in determining the appropriate femoral component size. The template includes anchoring pin holes for receiving anchoring pins therethrough and attaching the template to the femur distal end. Drill guide holes are also provided. The template is flat and generally U-shaped for slipping over an intramedullary rod.

20 Claims, 1 Drawing Sheet

FEMORAL SIZING APPARATUS

BACKGROUND OF THE INVENTION

The present invention relates generally to surgical devices used during knee surgery for the reinstatement of the natural knee joint. More particularly, the invention relates to a sizing apparatus wherethrough an appropriate size femoral component can be located and, thereafter, attached to the femoral distal end.

For various reasons, the human knee fails at the tibial and femoral juncture causing great pain and suffering to the individual. To correct this problem, surgeons now replace all or part of the natural knee joint with artificial components. Typically, a total knee replacement requires an artificial tibial component placed on the distal end of the tibia and an artificial femoral component placed at the distal end of the femur.

Because each individual's femur and tibia are different in size and because the extent of the damage to the tibia and femur distal ends cannot accurately be determined until after the knee has been cut open by the surgeon, the size of the implant components cannot easily be determined prior to the operation. Accordingly, it is common practice to initiate the operation, open up the knee, fully evaluate the needs of the patient and, at that time, determine the size of the femoral and tibial components. In view of this practice, manufacturers of femoral and tibial components typically manufacture five to eight different size components and arrange for all of their different sizes to be available to the surgeon during the operation. Accordingly, the surgeon must make a decision during the operation as to which of the different size components would best accommodate the patient's knee.

In the case of sizing the femoral distal end and determining which of the femoral component sizes to use, the common practice has been to measure the anterior to posterior distance of the femur and, utilizing this measurement, to pick an appropriate size femoral component. A typical device used by surgeons for measuring the anterior to posterior femoral distal end distance is shown at FIG. 1. As shown, the device includes a block having attached posterior arms. The posterior arms are placed on the back/underside portion of the femur condyles. The block further includes a vertically extending threaded rod upon which there is slidingly received an anterior arm or stylus. A nut member is threadingly received on the rod for engaging the anterior arm and forcing the anterior arm against an area proximal the intercondylar notch and toward the posterior arms. As shown in FIG. 1, during an operation, the surgeon places the device on the distal femoral end, tightens the bolt member, and directly reads the correct femoral component size for use on the patient.

Unfortunately, the prior art sizing component only takes into consideration the anterior to posterior distance somewhere further back from the distal condyles and does not take into consideration the medial to lateral distance, making it more difficult for the surgeon to determine the best fitting femoral component. Accordingly, the surgeon may initially utilize a femoral component that is either one size too large or one size too small, thereby requiring the surgeon to further reshape the femoral distal end to fit the chosen component.

Accordingly, there is a need for a femoral sizing device that better aids a surgeon in determining the appropriate size of femoral component.

SUMMARY OF THE INVENTION

The present invention overcomes any problems and disadvantages associated with the above-described prior art femoral sizing devices by providing a plurality of templates having both an anterior to posterior dimension and a medial to lateral dimension. The templates are generally flat and have anterior and posterior edges shaped in general conformity with the distal femoral condyles. A handle is attached to one of the template edges. Accordingly, during the operation, after the distal femoral cut is made and the end of the femur is made smooth using, for example, a circular hand rasp, the surgeon places the templates individually against the distal femoral end. The surgeon then views the templates against the distal femoral end, comparing the femoral distal end with the templates' anterior to posterior and medial to lateral dimensions. Rotation is also noted during this stage, for locating the template that best fits the femoral distal end. When the best fitting template is determined, the femoral component size corresponding to the specific template is obtained for use on the patient. As is evident, a femoral component size is more accurately obtained using the template of the present invention by comparing and noting both anterior to posterior and medial to lateral dimensions along with rotation.

In addition, the present invention provides templates that are generally U-shaped, including a central open section wherethrough an intramedullary rod may be received if the surgeon utilizes such a rod during surgery. Two anchor pin holes are also provided on the template wherethrough anchoring pins may be received for attaching the template to the distal femur end, if desired. Drill guide holes are also included on the template so that, after the template is anchored to the distal femur end, holes for receiving specific pegs provided on the femoral component may be drilled. Slots are also provided on the templates for use by the surgeon in viewing the location of the necessary cuts for the corresponding femoral component. A cutting block is then used to make the necessary cuts.

More specifically, the present invention provides, in one form thereof, a femoral sizing apparatus for determining the appropriate femoral component size. The apparatus includes a plurality of plates each having a specific anterior to posterior first dimension and a medial to lateral second dimension. The plates are for placement against a distal femur. Each of the plurality of plates correspond to a specific femoral component size. A handle may be attached to each of the plurality of plates for use in lifting and placing the plates against the distal femur. Accordingly, an appropriate corresponding femoral component is determined by viewing the plates against the distal femur and comparing the first and second dimensions against those of the distal femur. The plates are generally flat, U-shaped and include a central open section wherethrough an intramedullary rod may be received when the plates are placed against the distal femur. The plates can include a plurality of anchor pin holes for receiving anchoring pins therethrough and attaching the plates to the distal femur. The plates may also include a plurality of drill guide holes wherethrough a drill bit may be received for drilling holes in the distal femur. The plates include anterior, posterior, medial and lateral edges and the handle is attached to one of the edges. Preferably, the handles and plates are co-planar and the handles are attached by a welded or threaded connection. The anterior and posterior edges are most preferably shaped in general conformity with the distal femoral condyles. Slots may be provided for viewing the location of the needed anterior and posterior cuts to the distal femoral condyles.

A further aspect of the present invention, in one form thereof, is a method of sizing an appropriate femoral component using the apparatus of the present invention. The method includes first cutting off the distal femoral condyles. Thereafter, one of the plates best fitting the distal femoral end is located by grasping the handle and placing the plurality of plates individually against the femoral distal end and viewing the plates thereat and comparing the distal femoral end and the plates' first and second dimensions. Thereafter, a femoral component is identified corresponding to the located plate.

DESCRIPTION OF THE PREFERRED EMBODIMENT

Figure 1:
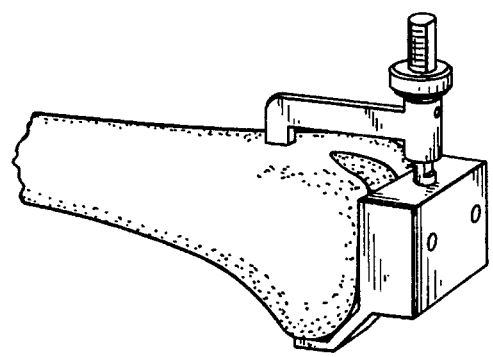
FIG. 1 is a perspective view of a femoral sizing device of the prior art placed on a femoral distal end.

In an exemplary embodiment of the invention as shown in the drawings, there is shown a femoral sizing apparatus generally indicated as 10. The apparatus includes a plurality of different sized plates or templates 12 (one shown) that are generally flat and have a handle 14 attached thereto. Each plate 12 includes an anterior edge 16, posterior edge 18, lateral edge 20 and medial edge 22. Handle 14 is attached to lateral edge 20 at an angle with respect to the lateral to medial direction. Handle 14 is co-planar with flat plate 12 and is attached to lateral edge 20 preferably by welding. Most preferably, handle 14 includes an end portion 24, shown in dashed lines, that is received within a bore 26, also shown in dashed lines. Handle 14 is thereafter welded along lateral edge 20 as shown at 28.

Handle 14 has a knurled surface for secure gripping thereof.

Each plate 12 is U-shaped and includes a central open section 30. Central open section 30 is provided for receiving therethrough an intramedullary rod used by some surgeons during the operation. Typically, the intramedullary rod is located longitudinally within the center of the femur. Central open section 30 is open toward posterior edge 18 so that the plates 12 can be easily slipped over an intramedullary rod when placing them against a distal femur.

Figure 2:
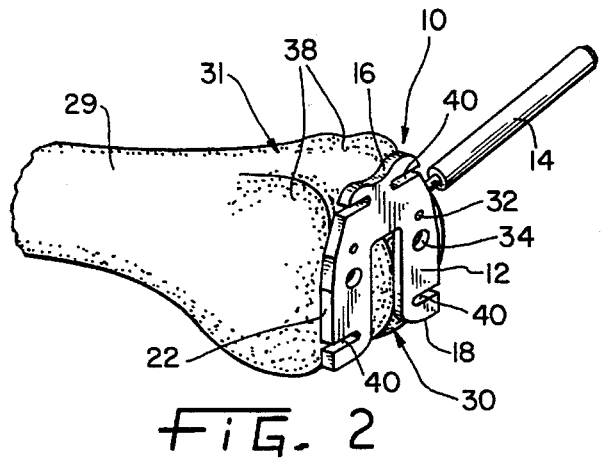
FIG. 2 is a perspective view of a femoral sizing apparatus in accordance with the principles of the present invention and placed against a femoral distal end.

Each plate 12 also includes anchoring pin holes 32 for receiving anchoring pins (not shown) therethrough. Various flanged anchoring pins can be used in conjunction with anchoring pin holes 32 for attaching a plate 12 against the femur distal end 31 as shown in FIG. 2.

In addition to anchoring pin holes 32 there are provided drill guide holes 34 wherethrough a drill bit may be received and guided for drilling holes in the longitudinal direction into the femur 29 from the distal end. Such holes may be used, for example, for receiving pegs (not shown) that are commonly provided on a femoral component 36 shown in FIG. 5.

Figure 3:
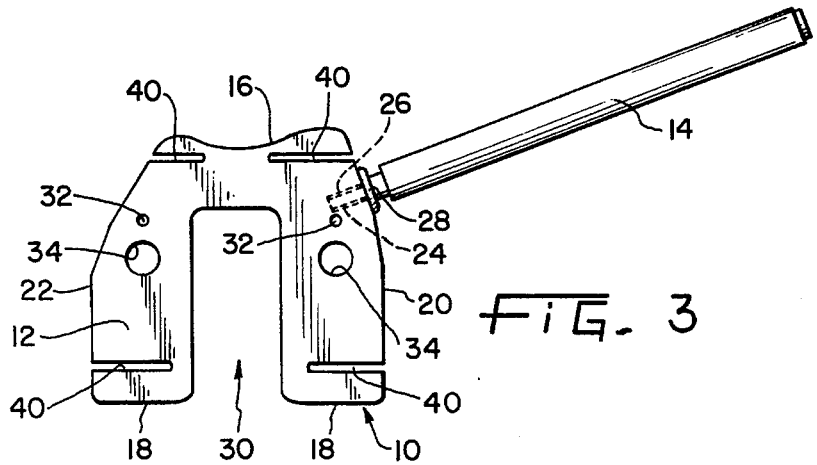
FIG. 3 is a top plan view of the femoral sizing apparatus of FIG. 2.

The plate edges 16, 18, 20 and 22 are most preferably shaped similar to a typical end view of a femoral distal end as shown in FIG. 3. More preferably, anterior edge 16 and posterior edge 18 are shaped, as shown, in general conformity with the distal femoral condyles 38. Near the anterior edge 16 and posterior edge 18 there are provided slots 40 that run in the lateral to medial direction. Slots 40 can be used after plate 12 is securely anchored to the femur distal end 31 for receiving a cutting instrument therethrough and guiding the cutting instrument for making the anterior and posterior cuts 42. More preferably, however, anterior and posterior slots 42 are only used for viewing the location of the needed anterior and posterior cuts for the corresponding specific femoral component 36. Here, a corresponding cutting block 44 can be attached to the femoral distal end for providing the necessary guiding surfaces in making not only the anterior and posterior cuts 42 but also the angled chamfer cuts 46.

As shown, plate 12 has a specific anterior to posterior first dimension and also has a medial to lateral second dimension. These first and second dimensions of each particular plate 12 correspond to a specific size of a femoral component 36. The apparatus thus preferably includes between five and eight different plates 12, each plate having a different specific anterior to posterior first dimension and medial to lateral second dimension. Each of these plates, in turn, correspond to a specific femoral component size.

Accordingly, during the operation, after the femoral and tibial distal ends are exposed, the surgeon first makes the distal femoral cut making the end of the femur generally flat. At that point, the femoral sizing apparatus 10 is used for determining the appropriate femoral component size. In this regard, a plate 12 is located by the surgeon that best fits a specific distal femoral end by grasping the handles 14 and individually placing the plurality of plates 12 against the distal femoral end as shown in FIG. 2. The surgeon views each individual plate noting the projection of the plate onto the distal femoral end. More specifically, the surgeon compares the aforementioned anterior to posterior dimension and lateral to medial dimension of each plate with the distal femoral end. Rotation of the plate is also noted in locating the most appropriate fitting femoral component. In addition, the surgeon notes the slots 40 and takes into consideration the portion of the distal condyles 38 that will have to be cut for the corresponding femoral component. It should be appreciated that plates 12, as shown in FIG. 3, can be viewed against either the left or the right femur of the patient by merely turning the plates 12 around and using the mirror image thereof. For example, in FIG. 3, the template outline is that of a right distal femoral end, whereas, its opposite mirror image is for the left distal femoral end. It is noted that during the locating of the plate that best fits the distal femoral end, if the surgeon has placed an intramedullary rod in the femur, the plates 12 are merely slipped thereover in a manner whereby the intramedullary rod is received through the central open section 30 of plates 12.

After the plate 12 that best fits the distal femoral end is located by the surgeon, the surgeon can and does identify the femoral component that corresponds to the best fitting plate for ultimate attachment to the femoral distal end. This is accomplished by corresponding markings on the plates 12 and the corresponding femoral components 36 or the packaging thereof. Any set of markings or identification system can be used for identifying and corresponding specific plates 12 with their corresponding specific femoral component size. Further, at this time, the surgeon may attach plate 12 to the femur distal end 31 using flanged anchor pins received through anchor pin holes 32 and placed into the femur distal end. After such attachment, holes can be drilled longitudinally into the distal femur end through drill guide holes 34. In addition, slots 40 can be used by inserting a cutting blade instrument therethrough and making the corresponding needed anterior and posterior cuts 42.

Figure 4:
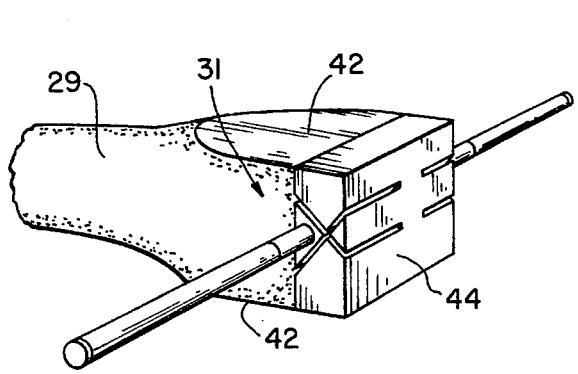
FIG. 4 is a perspective view of a typical cutting block attached to a femoral distal end for guiding a cutting instrument and making the necessary chamfering cuts; and, FIG. 5 is a perspective view showing a properly sized femoral component attached to a femur distal end after the various chamfering cuts have been made.
Figure 5:
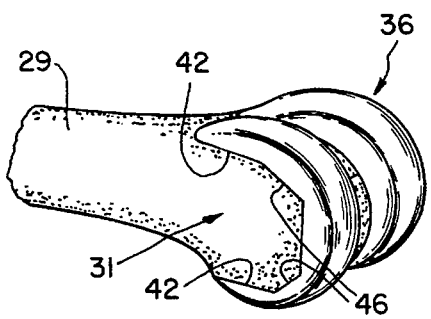

In the alternative, after the femoral component has been located as discussed hereinabove, a corresponding cutting block, such as that shown as 44 in FIG. 4, can be attached to the femur end and used for guiding the necessary cutting instruments and/or drill bits and creating the necessary cuts for properly fitting the femoral component 36 over the femur distal end 31 as shown in FIG. 5.

It will be appreciated that the foregoing description of a preferred embodiment of the invention is presented by way of illustration only and not by way of any limitation, and that various alternatives and modifications may be made to the illustrated embodiment without departing from the spirit and scope of the invention.

What is claimed is:

1. A femoral sizing apparatus for use by a surgeon in determining the appropriate femoral component size to be used in reconstructive surgery on the distal femur of a patient, said apparatus comprising:

a plurality of plate means, each having a specific anterior to posterior first dimension and a medial to lateral second dimension, for placement against the distal femur, each of said plurality of plate means corresponding to a specific femoral component size, and for viewing a projection of each plate means onto the distal femur and thereby determining the appropriate femoral component size.

2. The femoral sizing apparatus of claim 1 wherein each of said plate means are generally flat and U-shaped and include a central open section wherethrough an intramedullary rod may be received when said plate means are placed against the distal femur.

3. The femoral sizing apparatus of claim 1 wherein each of said plate means include a plurality of anchor pin holes for receiving anchoring pins therethrough and attaching said plate means to a distal femur.

4. The femoral sizing apparatus of claim 3 wherein each of said plate means include a plurality of drill guide holes wherethrough a drill bit may be received for drilling holes in the distal femur.

5. The femoral sizing apparatus of claim 1 wherein each of said plate means include a plurality of drill guide holes wherethrough a drill bit may be received for drilling holes in the distal femur.

6. The femoral sizing apparatus of claim 1 wherein each of said plate means include anterior and posterior edges shaped in general conformity with condyles of the distal femur.

7. The femoral sizing apparatus of claim 6 wherein each of said plate means includes guide slots at a location within the anterior to posterior first dimension whereat cuts to the distal femoral condyles corresponding to a specific femoral component are required, whereby the slots may receive a cutting instrument therethrough and guide the same to cut the condyles of the distal femur or permit viewing the location of needed cuts to aid in selecting the appropriate femoral component.

8. The femoral sizing apparatus of claim 1 wherein each of said plate means includes guide slots at a location within the anterior to posterior first dimension whereat cuts to the distal femoral condyles corresponding to a specific femoral component are required, whereby the slots may receive a cutting instrument therethrough and guide the same to cut the condyles of the distal femur or permit viewing the location of needed cuts to aid in selecting the appropriate femoral component.

9. The femoral sizing apparatus of claim 1 wherein each of said plate means includes handle means attached to each of said plurality of plate means for lifting and placing said plate means against a distal femur, whereby an appropriate corresponding femoral component is determined by viewing said plate means against the distal femur and comparing said first and second dimensions with those of the distal femur.

10. The femoral sizing apparatus of claim 9 wherein said plurality of plate means are generally flat and have anterior, posterior, medial and lateral edges, said handle attached at one of said edges.

11. The femoral sizing apparatus of claim 10 wherein said handle and plate means are co-planar.

12. The femoral sizing apparatus of claim 9 wherein said handle attachment is by welding.

13. A method of sizing an appropriate femoral component using an apparatus comprising a plurality of plates, each plate having a specific anterior to posterior first dimension and a medial to lateral second dimension, and each of said plates corresponding to a specific femoral component size, said method comprising:

locating one of the plates that best correspondingly fits a femoral distal end by placing said plurality of plates individually against the distal femoral end and viewing the plate thereat and comparing the distal femoral end and plate first and second dimensions; and, identifying a femoral component corresponding to said located plate for attachment to the femoral distal end.

14. The method of sizing an appropriate femoral component of claim 13 wherein the plates are generally flat and U-shaped having a central open section, and further comprising the steps of:

first placing an intramedullary rod within the femur and, thereafter, during the step of locating, individually placing said plurality of plates against the distal femoral end with the intramedullary rod received through the central plates central open sections.

15. The method of sizing an appropriate femoral component of claim 13 wherein each of the plates include two anchor pin holes and further comprising after the step of locating, placing anchoring pins through the plates anchor pin holes and attaching the located plate to the distal femur.

16. The method of sizing an appropriate femoral component of claim 15 wherein the plates include two drill guide holes and further comprising, after the step of placing anchoring pins, drilling holes in the distal femur through the drill guide holes.

17. The method of sizing an appropriate femoral component of claim 13 wherein the plates include two drill guide holes and further comprising, the step of drilling holes in the distal femur through the drill guide holes.

18. The method of sizing an appropriate femoral component of claim 13 wherein the plates include guide slots and further comprising, during the step of locating, the step of viewing the guide slots and ascertaining the location of needed cuts to the distal femoral condyles for the corresponding specific femoral component.

19. The method of sizing an appropriate femoral component of claim 13 further comprising prior to the step of locating, cutting off the distal femoral condyles and creating a flat surface area generally perpendicular to the longitudinal axis of the femur.

20. A femoral sizing apparatus for use by a surgeon in determining the appropriate femoral component size to be used in reconstructive surgery on the distal femur of a patient, said apparatus comprising:

a plate member having an anterior to posterior first dimension and a medial to lateral second dimension, said plate member being adapted for placement against the distal femur, said first and second dimensions corresponding to a specific femoral component size, whereby the surgeon views a projection of said plate member onto the distal femur and thereby determines the appropriate femoral component size.

* * * * *